United States Patent [19]

Hanifl et al.

[11] Patent Number: 4,715,545

[45] Date of Patent: Dec. 29, 1987

[54] TISSUE GRINDING AND TRANSPORT SYSTEM AND METHOD

[75] Inventors: Paul H. Hanifl, Barrington; John J. Newton, Jr., Palatine, both of Ill.

[73] Assignee: Sage Products, Inc., Cary, Ill.

[21] Appl. No.: 828,788

[22] Filed: Feb. 13, 1986

[51] Int. Cl.⁴ .............................................. B02C 23/36
[52] U.S. Cl. .................................. 241/169.1; 128/749; 206/222
[58] Field of Search ............ 241/46 R, 199.11–199.12, 241/169.1, DIG. 14, 169, 169.2, 199.8; 128/749; 206/222

[56] References Cited

U.S. PATENT DOCUMENTS

| | | | |
|---|---|---|---|
| 2,161,998 | 6/1939 | Chott | 241/169.2 X |
| 2,876,956 | 3/1959 | Bentley | 241/168 |
| 3,633,834 | 1/1972 | Nissen | 241/169.1 |
| 4,505,433 | 3/1985 | Selenke | 241/46 R |

Primary Examiner—Timothy V. Eley
Attorney, Agent, or Firm—Willian Brinks Olds Hofer Gilson & Lione Ltd.

[57] ABSTRACT

A system and method for collecting, transporting and grinding tissue specimens and the like which includes a long hollow container into which the sample of tissue is placed. A pestle or grinder of a shape to conform to the interior of the container is placed into the container in order to grind the sample. Attached to this grinder is a flexible protective sheath which envelops the grinder and container combination during grinding and thereby prevents contamination of the specimen or the surrounding atmosphere.

15 Claims, 4 Drawing Figures

TISSUE GRINDING AND TRANSPORT SYSTEM AND METHOD

FIELD OF THE INVENTION

The present invention relates generally to a system and method for grinding material, and more particularly to a system and method for grinding samples of tissue or the like, where the sample and the technician are protected from contamination during the collection, transporting and grinding stages, all of which may occur in the same container.

BACKGROUND OF THE INVENTION

In the many fields of microbiology, various types of containers and methods exist for the collection, testing and examination of tissue specimens. However, many containers and methods used in the testing of clinical specimens of tissue do not insure the safe and contamination-free collection, transport and grinding of the specimens. Historically, the containers in which the specimens were collected were designed without particular attention to grinding. Rather, the method used called for the collected tissue to be transferred to another vessel to accomplish the grinding operation.

This prior approach to tissue collection, transport and grinding presented a number of problems. One important problem concerned the chance of having the tissue samples become contaminated during the collection, transportation, or transfer process. Secondly, some of the prior systems and methods presented the possibility that the technician who collected, transported and ground the tissue specimen may become contaminated by the specimen. The possibility of contamination was particularly high when the grinding operation was conducted in open or inadequately shielded vessels.

These problems with some prior systems and methods underscored the need for a tissue collection system and method by which the samples could be safely collected, ground and transported in the same container, thus reducing the chance of contamination of the specimen or the technician. In addition, such a method would reduce the tediousness and time consumed by the entire collection, transporting and grinding task.

One prior system of collecting tissue samples is shown in Selenke, U.S. Pat. No. 4,505,433. There a cylindrical container for obtaining the sample was adapted to receive a grinder conforming to the cylindrical shape of this container. The grinder was compressible, and contained a pre-formed hollow chamber, where there was located a frangible glass ampoule of bacteria maintenance fluid. When a cap attached to the grinder was screwed down, the grinder itself would compress and the ampoule would break, thus preserving the tissue sample, which was ground during the process.

The prior art grinding methods also included the well-known ceramic or glass bowls, tubes or mortars and ceramic or glass rods or pestles.

Certain drawbacks were inherent in the method described in Selenke and in the use of conventional mortar and pestle arrangements. First, the Selenke system described was more complex than necessary. In effect, to insure the non-contamination of the tissue samples, the preservation system was built into the grinding apparatus. This made operation more costly than needed. Secondly, additional parts were needed in Selenke in order to insure the sterile handling of the sample. Not only was the grinder necessary, but the frangible ampoule and its protective sheath had to be included in the grinder. Finally, there was no insurance when using the Selenke device or the standard mortar and pestle that contamination of the specimen or the technician would not occur during the grinding stage. Since no provision was made for insuring that the tissue in the grinder was not exposed to the air, there was no provision for preventing any air-carried spores or bacteria from contaminating the sample or from being released from the sample and contaminating the technician.

The tissue grinding and transport system and method in accordance with this invention is designed to overcome the foregoing difficulties with prior systems and methods.

SUMMARY OF THE INVENTION

It is a primary object of the present invention to provide a system and method adapted for the collection, transport and grinding of tissue samples.

In recognition of the desire to preserve the sample in the same container during the entire collection, transportation and grinding phases, it is a further object of this invention to provide a system and method which is specifically adapted to receive a surgical tissue sample to allow for transport of the sample while it remains in the container, and to grind the sample while it is still in the container.

A further object of this invention is to provide a system and method that maintains the collected tissue sample in a non-contaminated environment which remains non-contaminated during the entire collecting, transporting and grinding phases.

A still further object of the invention is to provide a system and method for collecting, transporting and grinding tissue samples that will protect the nurse or technician from contamination.

These and other objects of the invention are accomplished in a system and method for collecting, transporting and grinding tissue or other solid material which includes a collection container having generally elongate outer walls defining a hollow interior chamber, and further having a closed bottom wall of a selected shape. The bottom wall forms a grinding surface on which to grind the tissue. In the preferred form of the invention the bottom wall is a converging grinding surface which is generally conical in configuration.

The system further includes a pestle or grinder which is adapted to be inserted into the hollow interior chamber created by the outer walls of the container. In the preferred embodiment the grinder is also hollow. The grinder includes a cylindrical sealing means adjacent the grinding surface which is formed to have a close fit to the interior walls of the collection container. The lower end forms a grinding surface, preferably conical in configuration, which corresponds to the interior conical surface of the collection container. The upper part of the grinder includes a double circular ring, which provides a groove for containing a flexible attaching means for attaching the protective sheath to the grinder. A handle or other suitable operating means are also provided to permit gripping and grinding. Grinding is effected by rotating the handle in either direction and/or using the handle to apply pressure to the specimen between the grinding surfaces. The upper portion of the grinder also preferably includes a second cylindrical seal to assist in sealing the opening between the grinder and the container.

The contamination-preventing sheath is a covering of thin flexible material, preferably a plastic sheet, which is formed in the shape of a long hollow cylinder. The sheath is attached to the grinder by use of a elastomeric retaining ring positioned over the sheath and grinder but between the double circular rings on the upper portion of the grinder. By allowing the sheath to pass over the container when the container is engaged with the grinder, the protective sheath can be compressed against the outer surface of the container to thereby prevent the contamination of the sample or the surrounding atmosphere during grinding.

In the preferred embodiment a cap is threaded to the top of the container. This cap is put in place to prevent contamination of the container during transport or storage of the tissue sample.

DETAILED DESCRIPTION OF THE INVENTION

Figure 1:
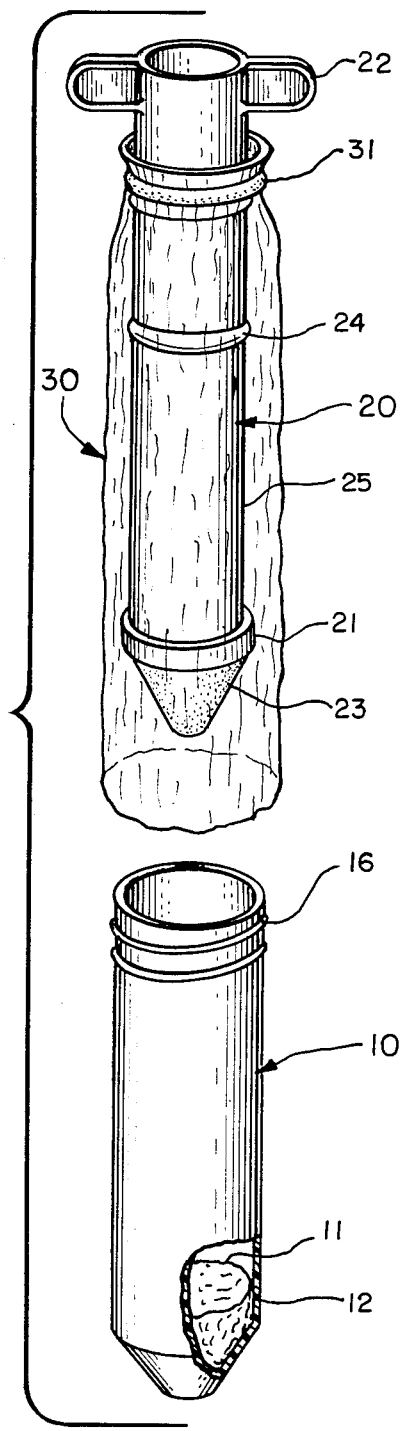
FIG. 1 is an exploded elevational view partly in section of the embodiment of a tissue collection, transport and grinding system made in accordance with this invention, showing the grinder with protective sheath attached and the collection container sectioned to show the tissue collected for grinding.

As shown in the drawings and for purposes of illustration, the collection, transport and grinding system of the present invention is generally indicated in FIG. 1. The system is primarily adapted to contain, transport and grind material such as a specimen or sample of surgical tissue, or the like and provides for the grinding of the material sample inside the collection container. The elements of the system comprise a container 10 having a hollow inside chamber 11 defined by the rigid wall 12. A grinder 20 having a grinding portion 23 fits into the chamber 11 of the container 10 and has an upper handle portion 22 that permits grinding of the tissue sample. The system further includes a protective sheath 30 which fits over the grinder and prevents contamination of the sample or the surrounding atmosphere during the grinding operation.

Figure 2:
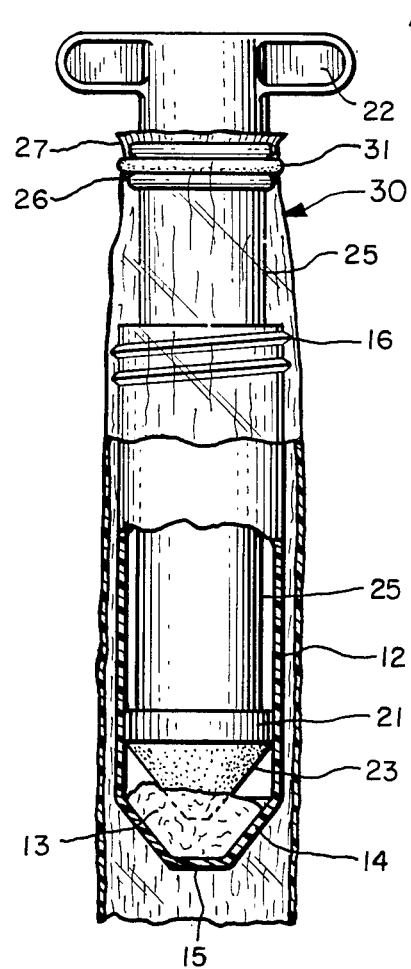
FIG. 2 is an elevational view partly in section of the assembled tissue grinding system.

The container 10 is preferably of a cylindrical shape and formed of a rigid plastic material. Its interior chamber 11 is also cylindrical in shape except for the grinding surface, and is defined by the rigid walls 12 of the container. As best seen in FIG. 2, the grinding surface 14 is generally in the shape of an inverse concave cone and is formed by sloping the bottom wall of the container. In the illustrated embodiment the conical grinding surface 14 is truncated to terminate in a plane surface 15. Again as seen in FIG. 1, the container 10 has pre-formed outer threads 16 which allow for the placement of a removable cap 40 over the container in order to prevent contamination during transportation or storage.

The grinder 20, which fits into the hollow chamber 11 of the container 10 is also formed of a rigid plastic and has three distinct portions. The lower end of the grinder 20 defines a circular sealing surface 21 and a conical grinding surface 23, formed to fit on the grinding surface 13 of the container 10. The sealing surface 21 is dimensioned to fit inside the hollow chamber 11 of the container 10 within a close tolerance to further prevent contaminants from getting to the tissue sample or prevent airborne particles of tissue from escaping during the grinding process. The grinder 20 is preferable also hollow so that the interior can receive ice or a coolant if the particular grinding operation requires the specimen to be kept at a lower temperature.

The intermediate portion 25 of the grinder 20 is also cylindrical in cross section. As seen in FIG. 2, the upper portion of the elongate cylindrical section 25 has two concentric rings 26 and 27, which are larger in cross section than cylindrical section 25 and are spaced to define a groove therebetween. By this arrangement an elastomeric retaining ring 31 can be secured between the rings 26 and 27. Connected to the top of the cylindrical portion 25 is a handle 22, formed to allow for ease of gripping by the person grinding the tissue sample. The upper portion 25 of the grinder also includes a second cylindrical seal 24 to further assist in sealing the container and grinder.

The protective sheath 30 is formed of a thin, flexible plastic sheet. This sheath 30 is also generally cylindrical in cross section. The sheath 30 forms a hollow flexible cylinder which fits over the container 10 when the grinder 20 is placed in the container 10. The protective sheath 30 is attached to the grinder 20 by the rubber retaining ring 31, which is placed over the sheath 30 and is retained between the concentric rings 26 and 27 of the grinder 20. The retaining ring 31 is of interior cross section larger than the diameter of the cylindrical portion 25 of the grinder 20, but smaller than the concentric rings 26 and 27 so that when forced over the concentric rings with the sheath 30 underneath it, the ring 31 snaps into place and will not move during the grinding process. However, in the preferred embodiment the elastomeric ring 31 is sufficiently flexible to permit the grinder 20 to rotate with respect to the sheath 30 during the grinding process.

Figure 4:
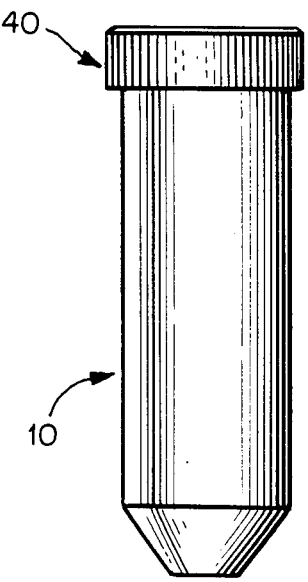
FIG. 4 is an elevational view of the container used in the tissue grinding system shown with a cap attached during transport or storage.
Figure 3:
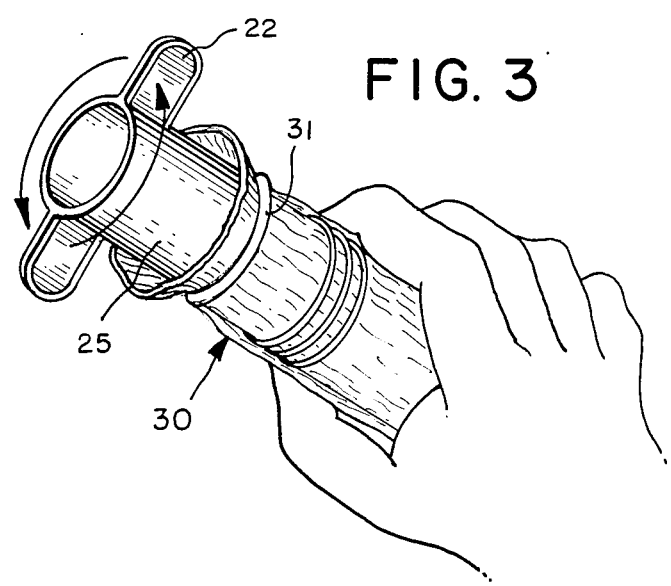
FIG. 3 is a perspective view illustrating the tissue grinding system during operation.

As seen in FIG. 4, a cap 40, also made of a rigid plastic, has inner threads not shown that are adapted to engage the outer threads 16 of the container 10, providing for easy, contamination free transport of the tissue samples.

To initiate the use of this system and method, a tissue sample is taken and placed into the hollow chamber 11 of the container 10 as seen in FIGS. 1 and 2. If the sample is to be transported or stored, the cap 40 can be placed on the container 10. Thereafter, the cap can be removed and the grinder 20 placed inside the container 10. Ice or coolant can be added to the interior of the grinder 20 if the application requires lower temperatures. During the process of placing the grinder 20 into the container 10 the sheath 30 envelops the grinder-container combination. In this manner, the tissue is doubly protected from contamination. First, the cylindrical seals 21 and 24 of the grinder reduce the probability of a contaminant entering the container 10 where the tissue is placed or the tissue contaminating the surrounding atmosphere. Secondly, the sheath 30 prevents any contamination by blocking any airborne spores and other bacteria from entering into the container 10.

In addition, the protective sheath 30 allows for contamination-free handling of the grinder 20 by the technician or analyst during the grinding phase by preventing any escape of tissue particles or the like from the container. To accomplish grinding while minimizing the possibility of contamination, the technician or analyst grinds the tissue by twisting the grinder 20 at the handle 22, while simultaneously pushing the grinder 20 into the container 10. The technician also compresses the flexible plastic protective sheath 30 against the container 10. The flexible sheet 30 conforms to the motion of the grinder by deflecting during the compressing action and twisting when the grinder 20 is rotated in the container 10 by the technician or analyst. The flexible retaining ring 31 also allows the grinder 20 to rotate with respect to the container 10 and the sheath 30 during the grinding operation.

After the grinding operation is completed, excess tissue which may be adhered to the grinding surface 23 of the grinder can be removed by partially withdrawing the grinder 20 to separate the two grinding surfaces. Then, the grinder and container combination can be oscillated or shaken to loosen the ground tissue from the grinder and discharge the tissue into the container.

When the tissue sample is fully ground, the system can be used for transporting or storing the sample. The technician carefully removes the grinder 20 from the container 10 by gripping the container 10 underneath the protective sheath 30. After removal of the grinder, the cap 40 is threaded onto the container 10. In this manner, the container is sealed from contaminants and easily transportable for further testing and analysis or storage. The used grinder and sheath assembly then can be discarded.

While the invention has been described in connection with a present preferred embodiment, it will be immediately obvious to those skilled in the art that many modifications of structure, arrangement, portions, elements, materials, and components used in the practice of the invention which are particularly adapted for specific environments are possible without departing from the principles of this invention.

What is claimed is:

1. A system for collecting and grinding tissue specimens or other biological samples comprise:
   an elongate container having an open top portion and rigid side walls defining a hollow interior for receiving the specimen and including a first grinding surface adjacent a bottom wall of the container;
   a grinder adapted for fitting into the open top portion of the container and including a second grinding surface engageable with the first grinding surface and further including operating means extending beyond the open top portion of the container when said grinding surface are engaged; and
   a protective sheath attached to the grinder and adapted to envelop and seal the opening between the container and the grinder with grinder emplaced within the container;
   whereby tissure specimens or other biological samples can be collected in said container and ground between said first and second grinding surfaces when said grinder is rotated within said container by the application of a rotating force to said operating means and said protective sheath thereby prevents the contamination of the specimen or the surrounding atmosphere during the grinding operation.

2. The system in accordance with claim 1 wherein the protective sheath comprises a flexible member attached to the grinder and adapted to extend across and surround said opening between the container and the grinder and further adapted to create a seal when compressed against the outer surface of the container.

3. The system in accordance with claim 2 wherein said grinder includes sealing means between said second grinding surface and said operating means which closely conforms to the side walls of the container when the grinder is emplaced within the container to assist in sealing the opening between the container and the grinder.

4. The system in accordance with claim 3 wherein said grinder includes a lower sealing means adjacent the second grinding surface and an upper sealing means adjacent the operating means to further assist the sealing of the juncture between the container and the grinder.

5. The system in accordance with claim 2 wherein said flexible sheath extends along substantially the full length of the container when the grinder is emplaced within the container.

6. The system in accordance with claim 2 wherein the flexible sheath is attached to the grinder by a yieldable attaching means which permits the grinder to be rotated with respect to said sheath while maintaining a seal between said sheath and said grinder.

7. The system in accordance with claim 6 wherein said attaching means comprises an elastomeric retainer engageable with said sheath within a groove defined in said grinder.

8. The system in accordance with claim 1 wherein said operating means comprises a handle for use in manually rotating the grinder within the container.

9. The system in accordance with claim 1 wherein the first grinding surface is defined by a concave bottom wall of said container and said second grinding surface comprises a conforming convex surface defined by the end of said grinder.

10. The system in accordance with claim 9 wherein said first and second grinding surfaces comprise conforming conical surfaces.

11. The system in accordance with claim 1 wherein the container includes a removable cap means for sealing the open top portion of the container.

12. The system in accordance with claim 11 wherein said cap is threadably attached to the top portion of said container.

13. The system in accordance with claim 1 wherein the interior of said grinder is hollow to receive ice or other coolant.

14. A system for collecting and grinding tissue specimens or other biological samples comprising:
   an elongate generally cylindrical container having an open top portion and rigid side wall defining a hollow interior for receiving the specimen and a bottom wall defining a first concave grinding surface;
   a generally cylindrical grinder adapted for fitting into the container and including a second convex grinding surface engageable with the first grindingf surface and further including operating means positioned beyond the open top portion of the container when said grinding surfaces are engaged; and
   a flexible protective sheath attached to the grinder and adapted to envelop and seal the opening between the container and the grinder by compression of the sheath against the outer surface of container with grinder emplaced within the container;

whereby a tissue specimen or other biological samples can be collected in said container and ground between said first and second grinding surfaces when said grinder is rotated within said container by the application of a rotating force to said operating means and said protective sheath thereby prevents the contaimination of the specimen or the surrounding atmosphere during the grinding operation.

15. The system in accordance with claim 14 wherein said sheath comprises a flexible plastic sheet material.

* * * * *

UNITED STATES PATENT AND TRADEMARK OFFICE
CERTIFICATE OF CORRECTION

PATENT NO. : 4,715,545
DATED : Dec. 29, 1987
INVENTOR(S) : Paul H. Hanifl et al.

It is certified that error appears in the above-identified patent and that said Letters Patent is hereby corrected as shown below:

IN THE SUMMARY OF THE INVENTION

In column 3, line 6, please delete "use of a" and substitute therefor --use of an--.

IN THE DETAILED DESCRIPTION OF THE INVENTION

In column 4, lines 8-9, please delete "preferable" and substitute therefor --preferably--;

In column 5, line 8, please delete "sheet" and substitute therefor --sheath--;

In column 5, line 33, please delete "present" and substitute therefor --presently--.

IN THE CLAIMS

In Claim 1 (column 5, line 42), please delete "comprise" and substitute therefor --comprising--;

In Claim 1 (column 5, line 52), please delete "surface" and substitute therefor --surfaces--;

UNITED STATES PATENT AND TRADEMARK OFFICE
CERTIFICATE OF CORRECTION

PATENT NO. : 4,715,545

DATED : Dec. 29, 1987

INVENTOR(S) : Paul H. Hanifl et al.

It is certified that error appears in the above-identified patent and that said Letters Patent is hereby corrected as shown below:

In Claim 1 (column 5, line 55), please delete "with grinder" and substitute therefor --with the grinder--;

In Claim 14 (column 6, line 53), please delete "side wall" and substitute therefor --side walls--;

In Claim 14 (column 6, line 59), please delete "grindingf" and substitute therefor --grinding--;

In Claim 14 (column 6, line 67), after "outer surface of" please insert --the--;

In Claim 14 (column 6, line 68), please delete "with grinder" and substitute therefor --with the grinder--.

Signed and Sealed this

Twenty-second Day of November, 1988

Attest:

DONALD J. QUIGG

*Attesting Officer*     *Commissioner of Patents and Trademarks*